US00PP09918P

United States Patent [19]

Wain

[11] Patent Number: Plant 9,918

[45] Date of Patent: Jun. 10, 1997

[54] CHRYSANTHEMUM PLANT NAMED 'IVORY FASHION TIME'

[75] Inventor: Peter Wain, Hayling Island, United Kingdom

[73] Assignee: Cleangro Limited, Chichester, United Kingdom

[21] Appl. No.: 627,462

[22] Filed: Apr. 4, 1996

[51] Int. Cl.[6] ..... A01H 5/00

[52] U.S. Cl. ..... Plt./77

[58] Field of Search ..... Plt./77

*Primary Examiner*—Howard J. Locker

*Attorney, Agent, or Firm*—C. A. Whealy

[57] ABSTRACT

A distinct cultivar of Chrysanthemum plant named Ivory Fashon Time, characterized by its flat capitulum form; vigorous and tall growth habit; freely branching plant habit; medium decorative-type inflorescences; pure white ray florets; numerous inflorescences per plant; numerous ray florets per inflorescence; and good postproduction longevity.

1 Drawing Sheet

The present invention relates to a new and distinct cultivar of Chrysanthemum plant, botanically known as *Dendranthema grandiflora* and referred to by the cultivar name Ivory Fashion Time.

The new cultivar is a spontaneous mutation of the commercial cultivar Fashion Time (U.S. Plant Patent application Ser. No. 08/627,606). The new cultivar was discovered and selected by the inventor in Havant, Hampshire, United Kingdom, as a single plant among a population of plants of the cultivar Fashion Time. This single plant consistently formed inflorescences having white-colored ray florets compared to the pink-colored ray florets of plants of the cultivar Fashion Time.

Asexual reproduction of the new cultivar by terminal cuttings taken at Havant, Hampshire, United Kingdom, has shown that the unique features of this new Chrysanthemum are stable and reproduced true to type in successive generations.

The following traits have been repeatedly observed and are determined to be the unique characteristics of Ivory Fashion Time. These characteristics in combination distinguish Ivory Fashion Time as a new and distinct cultivar:

1. Flat capitulum form.
2. Vigorous and tall growth habit.
3. Freely branching plant habit.
4. Medium decorative-type inflorescences.
5. Pure white ray florets.
6. Numerous inflorescences per plant.
7. Numerous ray florets per inflorescence.
8. Good postproduction longevity with inflorescences maintaining good substance and color for more than 18 days in an interior environment.

The cultivar Ivory Fashion Time has not been observed under all possible environmental conditions. The phenotype may vary somewhat with variations in environment such as temperature, daylength and light intensity, without, however, any variance in genotype.

Plants of the new Chrysanthemum are similar to the mutation parent cultivar Fashion Time in plant habit and growth rate. However in side-by-side comparisons in Oxnard, Calif., under commercial practice, plants of the new Chrysanthemum differed from plants of the cultivar Fashion Time in the following characteristics:

1. Plants of the new Chrysanthemum are shorter than plants of the cultivar Fashion Time.
2. Plants of the new Chrysanthemum are more freely branching than plants of the cultivar Fashion Time.
3. Plants of the new Chrysanthemum have smaller and shorter inflorescences than plants of the cultivar Fashion Time.

4. Ray florets of plants of the new Chrysanthemum are white in color, whereas ray florets of plants of the cultivar Fashion Time are pink in color.

A detailed comparison of plants of the new Chrysanthemum and the cultivar Fashion Time appears in Chart A at the end of the specification.

Plants of the new Chrysanthemum are similar to the cultivar Envy (disclosed in U.S. Plant Pat. No. 5,986) in ray floret color. However, in side-by-side comparisons conducted in Oxnard, Calif., under commercial practice, plants of the new Chrysanthemum differed from plants of the cultivar Envy in the following characteristics:

1. Plants of the new Chrysanthemum are taller, are more vigorous, and have longer lateral branches and peduncles than plants of the cultivar Envy.
2. Plants of the new Chrysanthemum are more freely branching and have more inflorescences per stem than plants of the cultivar Envy.
3. Leaves of plants of the new Chrysanthemum are shorter and narrower than leaves of plants of the cultivar Envy.
4. Inflorescences of plants of the new Chrysanthemum are smaller and slightly shorter than inflorescences of the cultivar Envy.
5. Ray florets of plants of the new Chrysanthemum are shorter and broader than ray florets of plants of the cultivar Envy.
6. The color of the opening ray florets on plants of the new Chrysanthemum is lighter yellow than opening ray florets of plants of the cultivar Envy.
7. Plants of the new Chrysanthemum have more ray florets and fewer disc florets per inflorescence than plants of the cultivar Envy.
8. Disc florets of plants of the new Chrysanthemum are shorter than disc florets of plants of the cultivar Envy.

A detailed comparison of plants of the new Chrysanthemum and the cultivar Envy appears in Chart B at the end of the specification.

The accompanying colored photograph illustrates the overall appearance of the new cultivar, showing the colors as true as it is reasonably possible to obtain in colored reproductions of this type. The photograph comprises a top perspective view of a typical flowering 16.5-cm container of Ivory Fashion Time with five cuttings in the container and the terminal inflorescences removed (center-budded pot chrysanthemum).

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with average night temperatures of 18° C., average day temperatures of 30° C., and light levels of 2,000 (cloudy conditions) to 9,000 (sunny conditions) footcandles.

After sticking unrooted cuttings of the new cultivar, plants received 21 long day/short nights followed by short day/long nights until flowering. Two weeks after the start of the short day/long night treatment, plants received four weekly spray applications of daminozide growth retardant at a rate of 2,500 ppm. Measurements and numerical values represent ranges or averages for six typical flowering plants.

Botanical classification: *Dendranthema grandiflora* cultivar Ivory Fashion Time.

Commercial classification: Decorative potted chrysanthemum.

Parentage: Spontaneous mutation of *Dendranthema grandiflora* cultivar Fashion Time (U.S. Plant patent application Ser. No. 08/627,606).

Propagation:

*Type.*—Terminal tip cuttings.

*Time to rooting.*—7 to 10 days with soil temperatures of 21° C.

*Rooting habit.*—Fine, fibrous and well-branched.

Plant description:

*Appearance.*—Perennial herbaceous decorative potted plant. Stems upright, uniform habit and freely branching. Vigorous growth habit.

*Plant height.*—25 to 26 cm.

*Lateral branch length.*—21 to 23 cm.

*Quantity of lateral branches after removal of apical meristem.*—About 4.

*Stem color.*—147B.

*Foliage description.*—Number of leaves per lateral branch: 16 to 17. Leaf arrangement: Alternate. Leaf size, fully expanded: Length: 11 to 12.5 cm. Width: 6 to 7 cm. Leaf apex: Acuminate. Leaf base: Attenuate. Leaf margin: Palmately lobed. Leaf texture: Upper and under surfaces slightly pubsecent, smooth and dull. Veins prominent on under surface. Petiole length: About 2 cm. Color: Young foliage upper surface: 147A. Young foliage under surface: 147B. Fully expanded foliage upper surface: 147A. Fully expanded foliage under surface: 147B. Venation upper surface: 147B. Venation under surface: 147B. Petiole: 147A.

Flowering description:

*Appearance.*—Decorative inflorescence form. Inflorescences borne on terminals above foliage, arising from leaf axils. Disc and ray florets arranged acropetally on a flat capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to 2 to 3 weeks of long day/short night conditions after sticking followed by photoinductive short day/long night conditions, flower about 55 to 57 days later.

*Postproduction longevity.*—In an interior environment, inflorescences and foliage of flowering plants will maintain good color and substance for at least 18 days in an interior environment.

*Quantity of inflorescences.*—8 to 10 inflorescences per flowering stem.

*Inflorescence size.*—Diameter: About 8 to 9 cm. Depth (height): About 2.7 cm. Diameter of disc: About 3 mm.

*Ray florets.*—Shape: Rounded, wide. Size: Length: 3.8 to 4.1 cm. Width: 1.4 to 1.6 cm. Apex: Rounded. Base: Acute. Margin: Entire. Texture: Satiny, smooth and glabrous. Aspect: Flat. Number of ray florets per inflorescence: About 330. Color: When opening, upper surface: 2D. When opening, under surface: 2D. Mature, upper surface: 155D. Mature, under surface: 155D.

*Disc florets.*—Shape: Tubular. Size: Length: About 4 mm. Width: About 1 mm. Number of disc florets per inflorescence: About 10. Color: Immature: 154A. Mature: 12A.

*Peduncle.*—Aspect: Strong and angled about 30° to the stem. Length: 6 to 7 cm. Texture: Glabrous. Color: 147B.

*Reproductive organs.*—Androecium: Present on disc florets only. Anther color: 12A. Pollen: Moderate, 12A in color. Gynoecium: Present on both ray and disc florets. Style color: 154A.

Disease resistance: No known Chrysanthemum diseases observed to date on plants grown under commercial greenhouse conditions.

Seed production: Seed production has not been observed.

CHART A

| CHARACTERISTIC | IVORY FASHION TIME | FASHION TIME |
|---|---|---|
| PLANT HEIGHT | 25 to 26 cm | 27.5 to 28 cm |
| QUANTITY OF LATERAL BRANCHES AFTER REMOVAL OF TERMINAL APEX | 4 | 3.5 |
| INFLORESCENCE DIAMETER | 8 to 9 cm | 9.5 to 10 cm |
| INFLORESCENCE DEPTH (HEIGHT) | About 2.7 cm | About 3.1 cm |
| RAY FLORET LENGTH | 3.8 to 4.1 cm | 4.7 to 5 cm |
| RAY FLORET COLOR, WHEN OPENING, UPPER SIDE | 2D | 62B |
| RAY FLORET COLOR, MATURE, UPPER SIDE | 155D | 62C |
| RAY FLORET COLOR, MATURE, UNDER SIDE | 155D | 62D |

CHART B

| CHARACTERISTIC | IVORY FASHION TIME | ENVY |
|---|---|---|
| PLANT HEIGHT | 25 to 26 cm | 23 to 24 cm |
| QUANTITY OF LATERAL BRANCHES AFTER REMOVAL OF TERMINAL APEX | 4 | 3 |
| LATERAL BRANCH LENGTH | 21 to 23 cm | 15 to 18 cm |
| VIGOR | Vigorous | Moderate |
| LEAF LENGTH | 11 to 12.5 cm | 12 to 14 cm |
| LEAF WIDTH | 6 to 7 cm | 6.5 to 8 cm |
| QUANTITY OF INFLORESCENCES PER STEM | 8 to 10 | 6 to 7 |
| INFLORESCENCE DIAMETER | 8 to 9 cm | 10 to 11 cm |
| INFLORESCENCE DEPTH | About 2.7 cm | About 2.8 cm |

-continued

CHART B

| CHARACTERISTIC | IVORY FASHION TIME | ENVY |
|---|---|---|
| (HEIGHT) | | |
| RAY FLORET LENGTH | 3.8 to 4.1 cm | 4.5 to 5.25 cm |
| RAY FLORET WIDTH | 1.4 to 1.6 cm | 1.1 to 1.3 cm |
| RAY FLORET COLOR, WHEN OPENING, UPPER SIDE | 2D | 7D |
| NUMBER OF RAY FLORETS PER INFLORESCENCE | About 330 | About 276 |
| DISC FLORET LENGTH | About 4 mm | About 6 mm |
| DISC FLORET QUANTITY | About 10 | About 44 |

-continued

CHART B

| CHARACTERISTIC | IVORY FASHION TIME | ENVY |
|---|---|---|
| PER INFLORESCENCE | | |
| DIAMETER OF DISC | About 3 mm | 7 to 9 mm |
| PEDUNCLE LENGTH | 6 to 7 cm | 3.5 to 4.5 cm |

It is claimed:

1. A new and distinct cultivar of Chrysanthemum plant named Ivory Fashion Time, as illustrated and described.

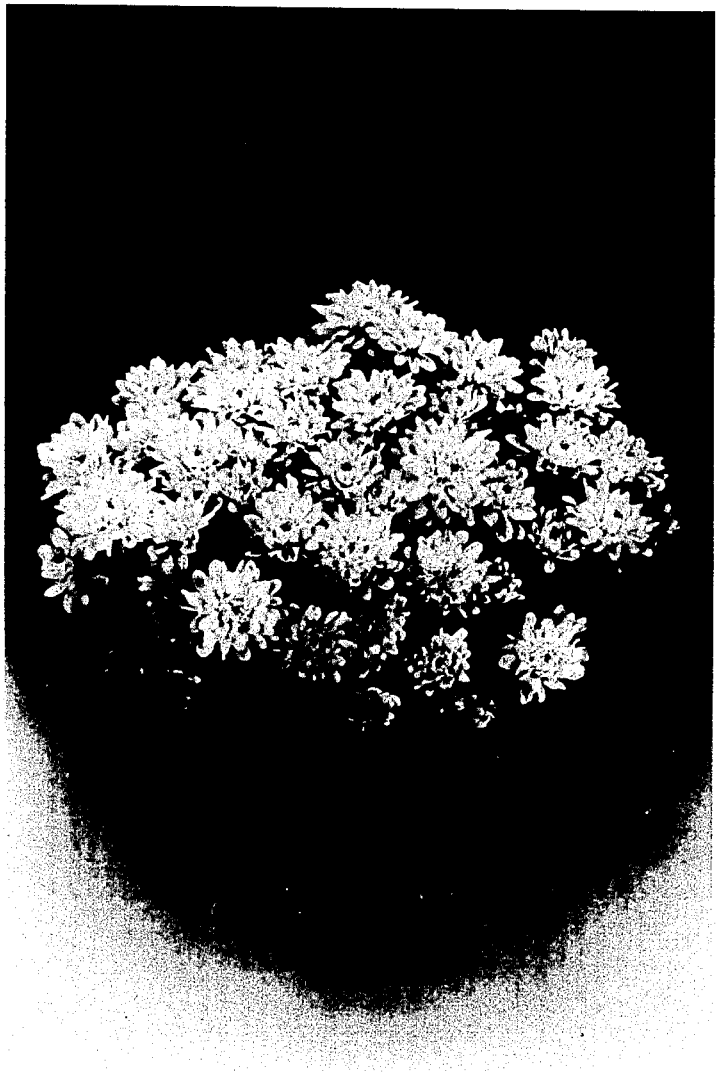

* * * * *